United States Patent [19]

Runge

[11] 4,302,854
[45] Dec. 1, 1981

[54] ELECTRICALLY ACTIVATED FERROMAGNETIC/DIAMAGNETIC VASCULAR SHUNT FOR LEFT VENTRICULAR ASSIST

[76] Inventor: Thomas M. Runge, 2501 Galewood Pl., Austin, Tex. 78703

[21] Appl. No.: 156,510
[22] Filed: Jun. 4, 1980
[51] Int. Cl.³ .................. A61F 1/24; A61M 1/03
[52] U.S. Cl. .................. 3/1.7; 128/1 D; 417/412
[58] Field of Search .................. 3/1.7; 128/1 D; 417/412

[56] References Cited

U.S. PATENT DOCUMENTS 3,733,616  5/1973  Willis, Jr. ..................... 3/1.7
4,014,318  3/1977  Dockum et al. ............... 3/1.7 X
4,143,425  3/1979  Runge ........................... 3/1.7

*Primary Examiner*—Ronald L. Frinks
*Attorney, Agent, or Firm*—B. P. Fishburne, Jr.

[57] ABSTRACT

A valved compressible state of the art Dacron shunt is sutured to the left atrium and to the descending thoracic aorta. One ferromagnetic and one diamagnetic shunt compression plate is positioned on one side of the shunt with the two plates in opposing relationship. A state of the art electromagnet and synchronizing mechanism exteriorly of the body cyclically, in accordance with the patient's QRS complex, generates a pulsating magnetic field which drives the ferromagnetic plate toward the diamagnetic plate, thereby cyclically compressing the shunt during diastole and giving assistance to the left ventricle of the heart.

3 Claims, 6 Drawing Figures

ELECTRICALLY ACTIVATED FERROMAGNETIC/DIAMAGNETIC VASCULAR SHUNT FOR LEFT VENTRICULAR ASSIST

BACKGROUND OF THE INVENTION

Left ventricular assist devices are known in the prior art as evidenced by U.S. Pat. No. 4,143,425, issued Mar. 13, 1979 to Runge. Such prior art devices include means for cyclically compressing a valved shunt connected between the left atrium and descending thoracic aorta. The shunt compression element is driven by a motor powered mechanism which includes a spirally grooved rotor or spinner and an axially movable ring follower connected to the spinner by a groove rider or follower. By this means, rotation of the spinner is converted to linear motion of the ring follower which directly operates the shunt compression element. Such a mechanism, while quite reliable, is subject to some of the inherent drawbacks of any mechanical device including gradual wear and friction which will ultimately limit the life of the mechanism.

The object of this invention is to improve on the known prior art through provision of an electrically activated ferromagnetic/diamagnetic vascular shunt cyclical compression means which can be synchronized with the patient's QRS complex by a power source wholly external to the patient's body. In accordance with the invention, mechanical drives, friction and wear are essentially eliminated along with all of the inherent disadvantages of purely mechanical systems. The invention is highly simplified, precise and reliable in operation. Its advantages should be readily apparent to those skilled in the art.

DETAILED DESCRIPTION

Figure 1:
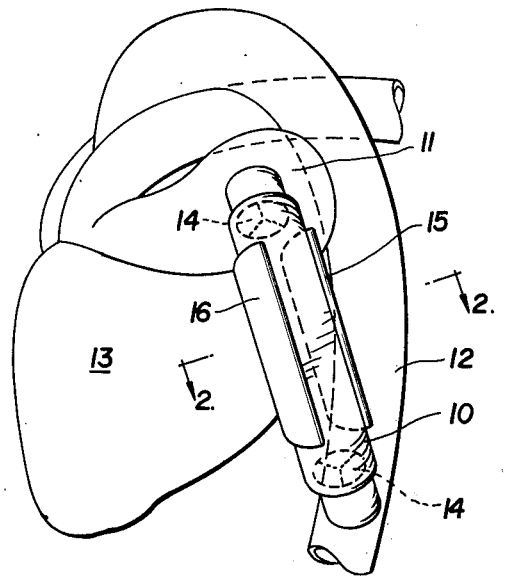
FIG. 1 is a partly diagrammatic perspective view of a left ventricular assist device in accordance with the present invention.

Referring to the drawings in detail wherein like numerals designate like parts, the numeral 10 designates a state of the art compressible Dacron shunt sutured to the left atrium 11 of the patient's heart and to the descending thoracic aorta 12, the left ventricle being indicated in FIG. 1 at 13. The shunt 10 is equipped with a pair of porcine valves 14 of the type specified in U.S. Pat. No. 4,143,425 near the points of attachment of the shunt to the heart and aorta. These check valves prevent back-flow of blood during the operation of the left ventricle assist device.

Figure 2:
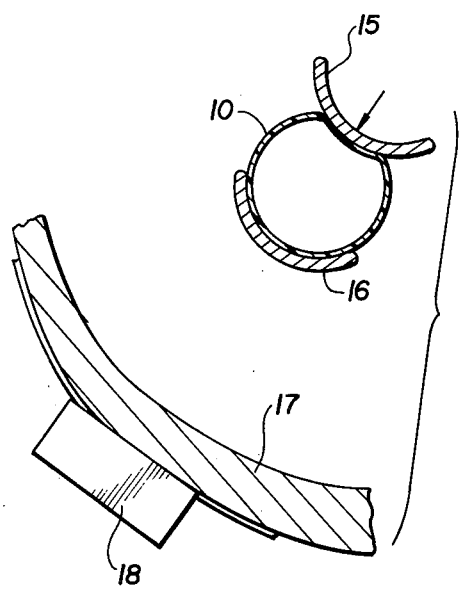
FIG. 2 is a partly schematic plan view in cross section through the device with the vascular shunt expanded as when full of blood.

An elongated arcuate shunt compression plate 15 formed of ferromagnetic material is placed within the chest cavity on the interior or distal side of the compressible shunt and a similar arcuate compression plate 16 formed of diamagnetic material is placed on the proximal side of the shunt 10 in relation to the chest wall 17 of the patient, as shown in FIG. 2. The implantation of the plates 15 and 16 is in accordance with known surgical procedures which need not be described in the application.

A power actuator means for the compression plates in the form of an electromagnet 18 is strapped to the exterior of the patient's chest in alignment with the two compression plates 15 and 16. The electromagnet actuator 18 is synchronized with the patient's QRS complex by a state of the art synchronization means, not shown.

Figure 3:
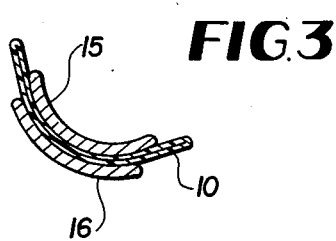
FIG. 3 is a similar view showing the shunt compressed to expel blood from the left atrium into the descending thoracic aorta in response to electrical activation of the device.
Figure 4:
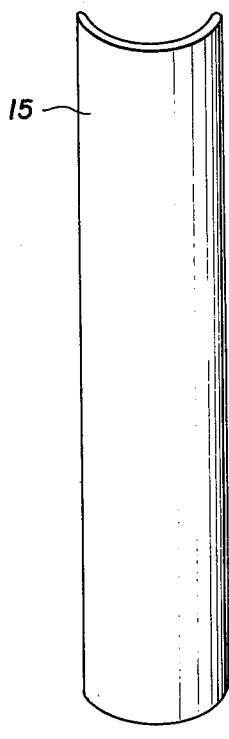
FIGS. 4 and 5 are perspective views of ferromagnetic and diamagnetic vascular shunt compression plates.
Figure 5:
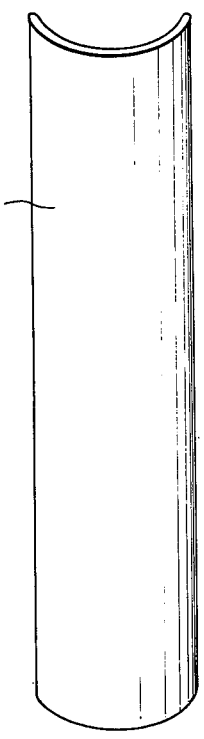
Figure 6:
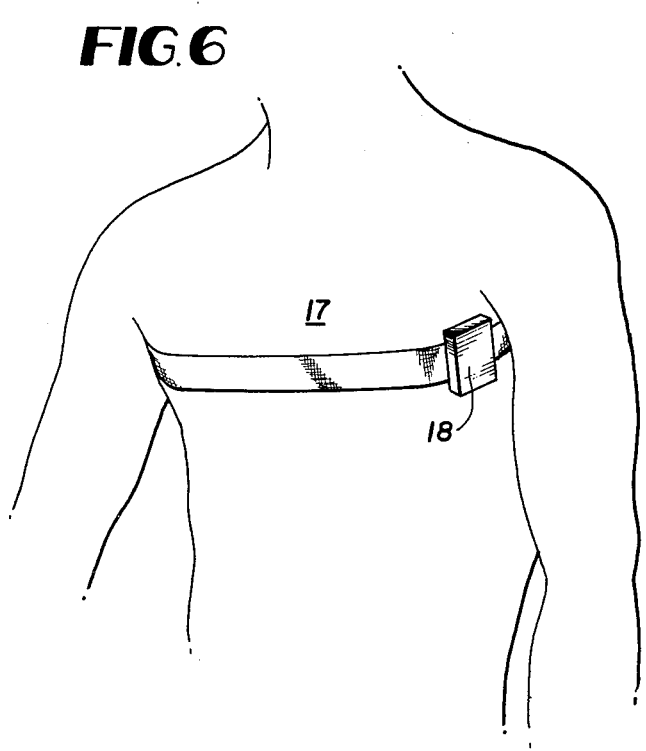
FIG. 6 is a perspective view of compression plate activating means on the exterior of the patient's body.

At the instant of left ventricular diastole, the electromagnet 18 creates an electromagnetic field which encompasses the ferromagnetic plate 15 and attracts or draws it toward the electromagnet 18, as shown by the arrow in FIG. 2. This magnetic attraction causes the feromagnetic plate 15 to move toward the relatively stationary diamagnetic plate 16 which has very little or no attraction to the electromagnet. As a consequence of this relative movement, the shunt 10 is squeezed and collapsed in the manner shown in FIG. 3 and the left atrium is unloaded of 50-100 cc. of blood per stroke, such blood being pumped into the descending thoracic aorta 12. The procedure is employed to assist a failing left ventricle of the heart.

The operation of the compression plates 15 and 16 is accomplished without linkage with the resulting friction and wear, as well as noise. The ferromagnetic plate, being electrically activated, moves with precision in a repetitive pumping cycle which can be timed and synchronized with diastole. The hardware implanted in the patient is minimized with obvious advantages to the patient. Simplicity and compactness of the device are fully achieved.

In lieu of the two valves 14 in the Dacron shunt 10, the device can be operated by using a single flutter valve of non-rigid design, such as a Shiley Laboratory valve.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A cardiac assist device comprising a valved compressible tubular shunt adapted for connection between a chamber of the heart and a coacting blood vessel, a pair of opposing shunt compressing plates of elongated form mounted on opposite sides of the shunt and extending lengthwise of the shunt for a major portion of its length between valves of the shunt, an electromagnetic actuator for the device adapted to be mounted on the exterior of the chest in lateral alignment with the shunt and said shunt compressing plates and generating an electromagnetic field in the vicinity of the shunt and shunt compressing plates, and one of the shunt compressing plates at the side of the shunt distal to said actuator being formed of ferromagnetic material and the other shunt compressing plate at the side of the shunt proximal to the actuator being formed of diamagnetic material, whereby the ferromagnetic compressing plate can cyclically be attracted by the field of said actuator toward the diamagnetic compressing plate to compress and collapse the entire portion of the shunt cyclically between the two compressing plates.

2. A cardiac assist device as defined in claim 1, wherein the two shunt compressing plates are of substantially equal lengths and arcuate in transverse cross section on substantially equal radii to match the cross sectional curvature of the shunt which is substantially cylindrical.

3. A cardiac assist device as defined in claim 2, and the electromagnetic actuator comprising an electromagnet adapted to have its activity synchronized with a user's QRS complex.

* * * * *